United States Patent [19]
Rickwood et al.

[11] Patent Number: 5,623,005
[45] Date of Patent: Apr. 22, 1997

[54] PHOTOCHROMIC NAPHTHOPYRAN COMPOUNDS

[75] Inventors: Martin Rickwood, Southport; Katharine E. Smith, Dewsbury; Christopher D. Gabbutt, Blackburn; John D. Hepworth, Preston, all of United Kingdom

[73] Assignee: Pilkington PLC, United Kingdom

[21] Appl. No.: 530,162

[22] PCT Filed: Mar. 25, 1994

[86] PCT No.: PCT/GB94/00628

§ 371 Date: Nov. 2, 1995

§ 102(e) Date: Nov. 2, 1995

[87] PCT Pub. No.: WO94/22850

PCT Pub. Date: Oct. 13, 1994

[30] Foreign Application Priority Data

Mar. 30, 1993 [GB] United Kingdom ............ 9306587

[51] Int. Cl.⁶ .................. C07D 405/02; C07D 413/02; G02B 5/23
[52] U.S. Cl. .................. 524/96; 524/99; 524/110; 252/586; 359/290; 523/106; 544/150; 544/70; 546/144; 546/196; 548/439; 548/454; 548/525; 548/409; 549/389; 428/913
[58] Field of Search ................. 544/150; 546/196; 549/389; 524/96

[56] References Cited

U.S. PATENT DOCUMENTS

| | | |
|---|---|---|
| 4,980,089 | 12/1990 | Heller . |
| 5,066,818 | 11/1991 | Gemert et al. . |
| 5,106,998 | 4/1992 | Tanaka et al. . |
| 5,384,077 | 1/1995 | Knowles ............ 549/389 |
| 5,543,533 | 8/1996 | Allegrini et al. ........ 549/389 |

FOREIGN PATENT DOCUMENTS

WO92/09593 6/1992 WIPO .

OTHER PUBLICATIONS

Chemical Abstract, vol. 96, No. 28, 1982, Columbus, OH, US; Abstract No. 69027 Abstract (Otsuka Pharmaceuticals.), JP,A,8 149 361, May 2, 1981.

*Primary Examiner*—Robert W. Ramsuer
*Attorney, Agent, or Firm*—Burns, Doane, Swecker & Mathis LLP

[57] ABSTRACT

A naphthopyran compound of general formula (I)

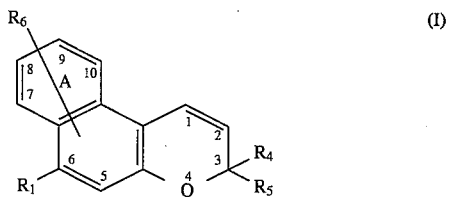

wherein $R_1$ represents a group of the formula $-NR_2R_3$ wherein each of $R_2$ and $R_3$, which may be the same or different, independently represents an alkyl group, or a carbocyclic or heterocyclic group, or $R_2$ and $R_3$ taken together with the nitrogen atom to which they are attached represent a heterocyclic ring having one or more hetero atoms and which may optionally carry at least one substituent selected from alkyl, aryl, or heteroaryl groups; each of $R_4$ and $R_5$, which may be the same or different, independently represents an alkyl, alkenyl, carbocyclic or heterocyclic group, or $R_4$ and $R_5$ taken together with the carbon atom to which they are attached form a carboxylcyclic ring or a heterocyclic ring; and $R_6$ represents a hydrogen atom or a substituent selected from alkyl, alkoxy, aryl, aryloxy, heteroaryl, halogen, a group of formula $R_1$ as defined above, azo, imino, amide, carboxylate, ester, cyano, trifluoromethyl or nitro, and in addition $R_6$ may represent a carbocyclic or heterocyclic ring fused to ring A. The naphthopyran compounds of the invention are useful as photochromic materials in lenses, e.g. sunglasses, and photochromic transparencies for cars and aircraft. The invention also provides, as new intermediate compounds, amine-substituted chloronaphthols and amine-substituted naphthols.

23 Claims, No Drawings

PHOTOCHROMIC NAPHTHOPYRAN COMPOUNDS

This application is a 371 of PCT/GB94/00628 filed Mar. 25, 1994.

The present invention relates to certain novel photochromic naphthopyran compounds, and to articles and compositions containing them.

Photochromism is a well-known physical phenomenon which is observed with certain classes of chemical compounds. A detailed discussion of this phenomenon can be found in "Photochromism: Molecules and Systems", Studies in Organic Chemistry 40, Edited by H. Durr and H. Bouas-Laurent, Elsevier 1990.

Naphthopyran compounds as a class of compounds are known to be capable of exhibiting a photochromic effect. For example, U.S. Pat. No. 4,980,089 describes a series of photochromic naphthospiropyran compounds containing a norcamphor group or a tricyclodecane group at the 2-position of the naphthospiropyran ring (This 2-position corresponds to the 3-position of the ring in the numbering system used in the present specification).

A series of novel reversible photochromic naphthopyran compounds carrying an acetoxy group (or analogues thereof) at the 5-position of the naphthopyran ring is described in WO 92/09503.

U.S. Pat. No. 5,106,998 describes a variety of photochromic compounds including various naphthopyran compounds of different structures.

U.S. Pat. No. 5,066,818 describes a group of novel reversible photochromic naphthopyran compounds having at least one ortho-substituted phenyl group at the 3-position of the pyran ring.

We have now found a group of naphthopyran compounds which provide substantially greater induced optical density in their darkened state than other known naphthopyran compounds. The common characteristic of the novel naphthopyran compounds of the present invention is that they carry a substituted amino group in the 6-position of the molecule.

Accordingly, the present invention provides a naphthopyran compound of general formula (I)

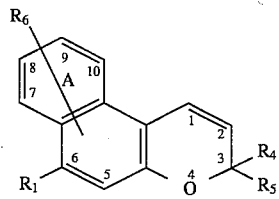

(I)

wherein $R_1$ represents a group of the formula —$NR_2R_3$
wherein each of $R_2$ and $R_3$, which may be the same or different, independently represents an alkyl group, or a carbocyclic group, preferably aryl, or a heterocyclic group, or $R_2$ and $R_3$ taken together with the nitrogen atom to which they are attached represent a heterocyclic ring having one or more hetero atoms and which may optionally carry at least one substituent selected from alkyl, aryl or heteroaryl groups;
each of $R_4$ and $R_5$, which may be the same or different, independently represents an alkyl, alkenyl, carbocyclic or heterocyclic group, or $R_4$ and $R_5$ taken together with the carbon atom to which they are attached form a carbocyclic ring or a heterocyclic ring; and $R_6$ represents a hydrogen atom or a substituent selected from alkyl, alkoxy, aryl, aryloxy, heteroaryl, halogen, a group of formula $R_1$ as defined above, azo, imino, amide, carboxylate, ester, cyano, trifluoromethyl or nitro, and in addition $R_6$ may represent a carbocyclic or heterocyclic ring fused to ring A.

Throughout this specification, unless stated otherwise, the term "alkyl" is to be taken to mean an alkyl group having from 1 to 4 carbon atoms. Similarly, the term "alkoxy" is to be taken to mean an alkoxy group having from 1 to 4 carbon atoms.

Furthermore, in the definitions of $R_1$, $R_4$, $R_5$ and $R_6$ above, whenever reference has been made to a carbocyclic or heterocyclic ring (or group), unless specified otherwise it is to be understood that such carbocyclic or heterocyclic rings (or groups) may be unsubstituted or may carry one or more substituents chosen from halogen atoms, alkyl, alkoxy, aryl, aryloxy, heteroaryl, amino, a group —$NR_2R_3$ as defined above, azo, imino, amide, carboxylate, ester, cyano, trifluoromethyl or nitro groups, or, further, such rings may have one or more further rings which are fused thereto.

For the avoidance of doubt, in the definition of $R_1$ above, the group —$NR_2R_3$ includes within its scope ring systems in which one or more further rings are fused to the heterocyclic ring, and such ring systems may incorporate saturated and/or unsaturated rings. Typical examples of such —$NR_2R_3$ groups include a tetrahydroisoquinoline substituent of formula:

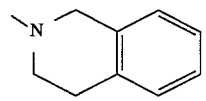

or an indoline substituent of formula

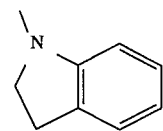

or a hexahydrocarbazole substituent of formula

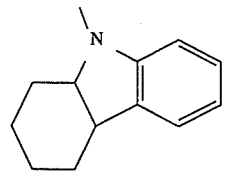

In the compounds of formula (I), ring A may carry more than one substituent $R_6$.

In a group of preferred compounds in accordance with the invention, the $R_1$ substituent is a piperidino group, a morpholino group or an N-methyl piperazino group.

Preferably, the substituents $R_4$ and $R_5$ on the pyran ring are chosen from a phenyl group, a 4-trifluoromethyl-phenyl group, a 4-alkoxyphenyl group (preferably 4-methoxyphenyl), a 2,4-di(alkoxy)phenyl group (preferably 2,4-dimethoxyphenyl) or a 4-dialkylamino-phenyl group (preferably 4-dimethylamino-phenyl).

Alternatively, the $R_4$ and $R_5$ substituents together with the carbon atom to which they are attached form a spiroindoline group carrying alkyl or aryl substituents or alicyclic $C_{1-18}$ groups at the 1-, 3-, 3-positions of the indoline ring. The alkyl groups may be linear or branched, and may have up to 18 carbon atoms. If desired, the aromatic ring of the indoline group may carry one or more substituents which are substituents as defined for $R_6$ above.

It is also envisaged that the advantageous properties of the compounds of the present invention will be obtained with a compound of general formula (I) in which the $R_4$ and $R_5$ substituents together with the carbon atom to which they are attached form a spiro-adamantylidene group.

The naphthopyran compounds of the present invention may be prepared by a general preparative method which is based on the following reaction scheme:

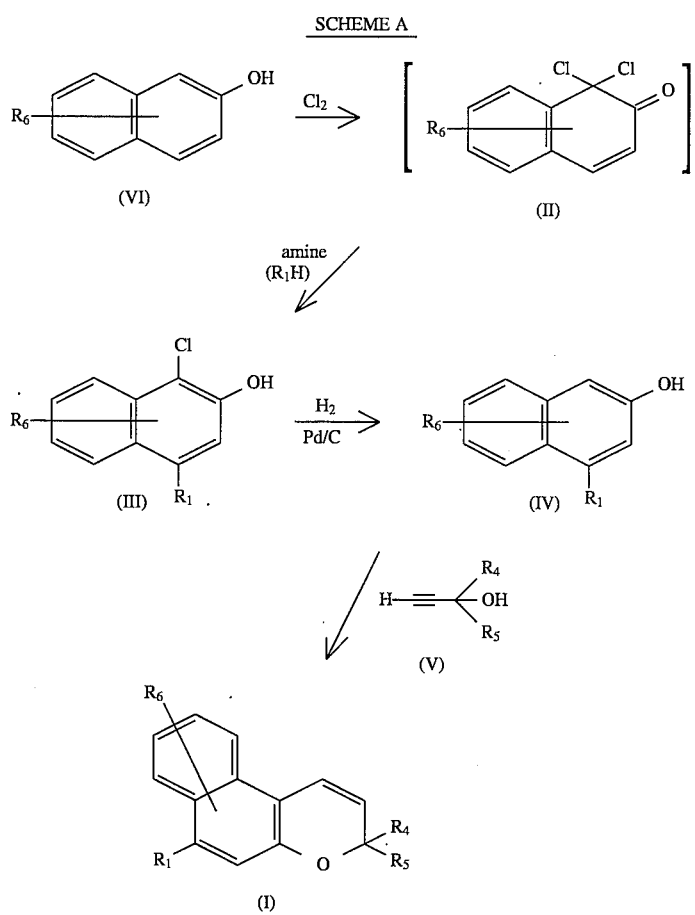

The compounds of formula (I) in which $R_4$ and $R_5$ taken together represent a spiro-indoline group are made by a slightly different synthetic route, as shown in the following reaction scheme:

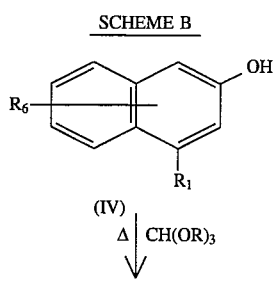

-continued
SCHEME B

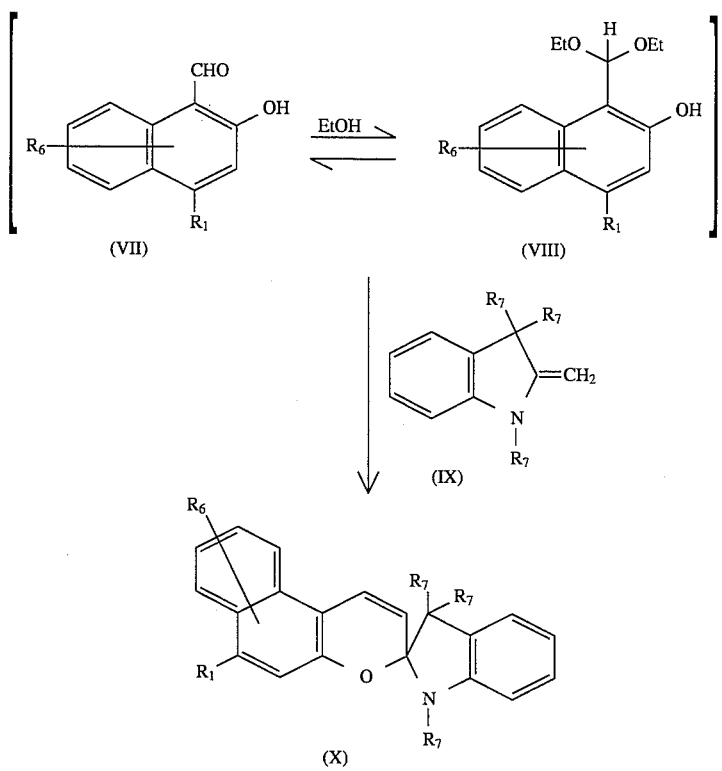

Accordingly, the present invention also provides a process for preparing a naphthopyran compound of general formula (I) as defined above, which process comprises (a) chlorinating a solution of a 2-naphthol of general formula (VI):

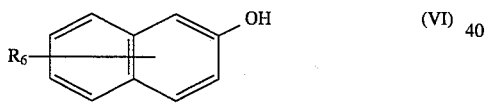

wherein $R_6$ is as defined above, in an organic solvent to produce the corresponding 1,1-dichloronaphth-2-one which is reacted with an amine of general formula $R_1H$ in the presence of an organic base (typically, a tertiary amine such as triethylamine) to generate a chloro-naphthol of general formula (III):

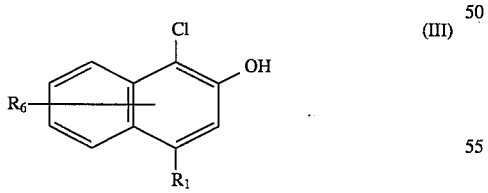

(b) subjecting the chloro-naphthol of general formula (III) to a hydrodehalogenation reaction to produce a substituted naphthol of general formula (IV):

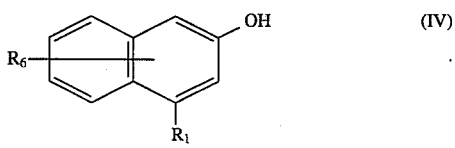

and then either:

(c) condensing the substituted naphthol of general formula (IV) with a propargyl alcohol of general formula (V):

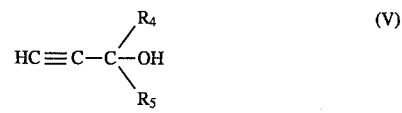

wherein $R_4$ and $R_5$ are as defined above, in the presence of acidic alumina, trifluoroacetic acid or another like acidic catalyst, or (c') when $R_4$ and $R_5$ together with the carbon atom to which they are attached form a spiro-indoline group, condensing the substituted naphthol of general formula (IV) with a 2-alkylidene indole of general formula (IX):

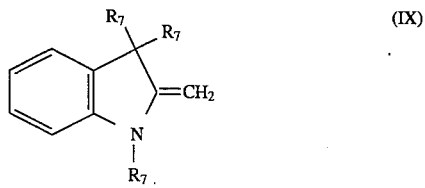

wherein $R_7$ represents an alkyl group or an aryl group or an alicyclic $C_{1-18}$ group, in the presence of a trialkyl orthoformate.

In the preparation processes described above, 1,1-dichloronaphth-2-one(II) is first prepared from 2-naphthol(VI) by a method derived from the process described by G. M. Iskander et. al. in J. Chem. Soc. (C), 1970, 1701–1703.

Thus, 1,1-dichloronaphth-2-one (II) is produced in good yield from the direct chlorination of 2-naphthol. The chlorination is carried out by vigorously bubbling chlorine through a stirred naphthol solution in a solvent such as chloroform, carbon tetrachloride, benzene, diethyl ether or toluene, at room temperature, at a relatively fast rate (e.g.

2–3 g/min for a 0.1 mol scale reaction) until a two-fold excess of chlorine has been added. The use of a two-fold excess of chlorine is important in so far that yields are kept high and the production of unwanted by-products is kept to a minimum thereby avoiding the need for isolation and purification of the dichloro compound (II) after this particular step. On completion of the chlorination, nitrogen is bubbled through the stirred solution at a fast rate in order to drive off any excess chlorine and also to clear the solution of hydrogen chloride produced during the reaction. Hydrogen chloride is known to react with the 1,1-dichloronaphthone at elevated temperatures thereby causing a yield reduction. The majority of the HCl is driven off during the reaction.

We have discovered that the dichloro compound (II) is extremely labile to attack at the 4-position by amines resulting in the formation of 4-amine-substituted 1-chloro-2-naphthols of formula (III) and HCl, the latter being removed by filtration as a tertiary amine/HCl salt (e.g. triethylamine hydrochloride).

In general, the 4-amine-substituted compounds of formula (III) are prepared by first adding a molar excess of an organic base such as triethylamine in one portion to the solution of the dichloro compound (II) followed by the controlled addition of a slight excess (e.g. 10%) of secondary amine of formula $R_1H$ (e.g. piperidine), whilst maintaining the overall reaction temperature below 25° C. The resulting mixture is filtered to remove any precipitated amine/HCl salt and the filtrate washed with water to remove any remaining salt and the dried filtrate evaporated to yield the chloroaminonaphthol of formula (III).

The hydro-dehalogenation of the aminochloronaphthols of formula (III) to generate the 4-amino-2-naphthols of formula (IV) can be carried out using a number of well-known reagents and conditions (e.g. Raney-Nickel) but the preferred method is by catalytic medium-pressure hydrogenation under basic conditions, for example aqueous KOH or NaOH. A typical catalyst is 5% Pd on charcoal. The hydro-dehalogenation step may be carried out on relatively impure aminochloronaphthols but impurities may poison the catalyst thereby reducing the yields. The 4-amino-2-naphthol compounds of formula (IV) are formed in moderate to good yields.

The synthesis of naphthopyran compounds from naphthols is generally well known and is described in detail, for example, by L. Merlini in Advances in Heterocyclic Chemistry, 1975, 18, 159 and in a number of patents, for example, U.S. Pat. No. 5,066,818, U.S. Pat. No. 4,990,287, U.S. Pat. No. 4,980,089 and WO 92/09593. Typically, in the process of the present invention, the formation of the 3,3-disubstituted and 3-spiro-carbocyclic naphthopyrans takes place via an initial condensation/etherification reaction between an amino-naphthol of general formula (IV) and a propargyl alcohol of general formula (V) in the presence of acidic alumina (e.g. Brockmann 1 alumina), trifluoroacetic acid or other like acidic catalyst.

Compounds of the general formula (I) having a spiro-indoline substituent at position 3 (e.g. compound (X) in Scheme B) are made by a different synthetic route as illustrated in Scheme B above. The preparation of these materials can be performed by a one-pot reaction in which an amino-naphthol of general formula (IV) is reacted with a 2-alkylideneindote of general formula (IX) in the presence of a trialkylorthoformate, e.g. triethylorthoformate. The general mechanism and synthesis of such spiroheterocyclo-naphthopyrans is described more fully by H. Durr and H. Bouas-Laurent in Studies in Organic Chemistry 40; Photochromism:Molecules and Systems, Elsevier 1990, chapter 8, 419–451.

The novel naphthopyran compounds of the present invention are found to be particularly useful as photochromic materials to be incorporated into polymeric host materials so as to impart photochromic properties to the said polymeric host materials.

The photochromic naphthopyran compounds of the present invention are incorporated into the plastics host material in known manner, for example as described in European Patent No. 0245020 or U.S. Pat. No. 5,066,818.

The naphthopyran compounds of the invention exhibit substantially greater induced optical density (IOD) than prior art materials of comparable structure. As a result, the amount of photochromic material required to impart a useful degree of photochromism to a polymeric host material or to a solution is greatly reduced when compared to the amount required to obtain an equivalent photochromic effect with prior art photochromic materials.

The use of reduced quantities of the photochromic materials of the invention not only gives a saving in cost, but also has the added advantage that there is a consequent reduction in any undesirable colour that the photochromic materials may impart in the bleached state, either by way of the inherent colour of the photochromic material itself, or by way of any coloured degradation/fatigue products that may be generated during use of the photochromic material.

A further advantage of the photochromic naphthopyran materials of the present invention is that they exhibit a fatigue performance which is as good as, if not better than, known photochromic compounds of similar structure.

The colour range of the naphthopyrans of the present invention is 400 to 550 nm; thus, the materials of the present invention impart a yellow or orange or red or red-purple colouration in their darkened state. In the faded or bleached condition the materials exhibit a colourless or pale colouration.

Typical polymeric host materials are optically clear polymer materials, such as polymers of polyol(allyl carbonate)-monomers, polyacrylates such as polymethylmethacrylates, cellulose acetate, cellulose triacetate, cellulose acetate propionate, cellulose acetate butyrate, poly(vinyl acetate), poly(vinyl alcohol), polyurethanes, polycarbonates, polyethylene terephthalate, polystyrene, styrene/methylmethacrylate copolymers, styrene/acrylonitrile copolymers, and polyvinylbutyral. Transparent copolymers and blends of the transparent polymers are also suitable as host materials. Polymers of the type described in EP 0453149 are also suitable.

Preferably, the polymeric host material is an optically clear polymerized organic material such as a polymer of triethylene glycol dimethacrylate (TEGDM) or a polymer of diethylene glycol bis(allyl carbonate) (sold under the trade name CR-39), or SPECTRALITE—a material sold by Sola Optical USA.

Usually, the amount of photochromic naphthopyran compound incorporated in the polymeric host material ranges from 0.001 to 0.1 wt %, based on the weight of the polymeric host material.

In some applications, it may be desirable or advantageous to combine the naphthopyran compounds of the present invention with other photochromic materials to obtain an aggregate colour effect. For example, spiro-oxazine materials may have a colour range of 530 to 680 nm which means that in the darkened condition the spiro-oxazines impart a red-purple or purple or blue or blue-green or green colouration to a host material. Thus, the present naphthopyran compounds are complementary to known spiro-oxazine materials such as those described in our European Patent No. 0245020, or in our UK Patent Applications Nos. 92/25346, 92/25347 and 92/25348, or to the spiro (indolino) naphthoxazines, spiro (indolino) pyrido benzoxazines and spiro (indolino) benzoxazines described in U.S. Pat. Nos. 4,637, 698, 3,562,172, 3,578,602, 4,816,584, 4,215,010 and 4,342, 668, and can be combined with such other photochromic materials.

Typically, when used in combination, the further additional photochromic material is present in an amount of from 0.001 to 0.5 weight % based on the weight of the polymeric host material.

Examples of suitable uses of the photochromic plastic articles incorporating the naphthopyran compounds of the invention are in the manufacture of plano lenses, e.g. for sunglasses, and ophthalmic lenses and as photochromic transparencies for vehicles such as cars and aircraft.

Some of the intermediate compounds used to prepare the naphthopyran compounds of the invention are themselves new compounds.

According to a further aspect of the present invention there is provided a chloro-naphthol compound of general formula (III):

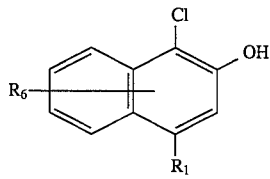

wherein $R_1$ and $R_6$ are as defined above.

According to a still further aspect of the present invention there is provided a naphthol compound of general formula (IV)

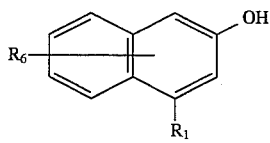

wherein $R_1$ and $R_6$ are as defined above, with the proviso that $R_1$ is not $-N(CH_3)_2$.

The preparation of these intermediate compounds has been described above in general terms in the description of the processes for preparing the naphthopyran compounds of general formula (I) with reference to Scheme A, and more detailed preparative methods of these intermediates are given in the following Examples.

The following Examples illustrate the present invention.

EXAMPLE 1

3,3-Dianisyl-6-piperidino-3H-naphtho[2,1-b]pyran.
(a) 1-Chloro-4-piperidino-2-naphthol 2-Naphthol (28.8 g; 0.200 mol) was dissolved in toluene (210 ml) by warming. The pale brown solution was cooled and vigorously stirred until the naphthol began to precipitate and chlorine (30.20 g;0.425 mol) was then passed through the solution at approximately 2.5–3.0 g/min followed immediately by nitrogen gas. The resulting amber solution was treated firstly with triethylamine (24.68 g;0.244 mol) in one portion and then with a solution of piperidine (19.55 g;0.230 mol), in toluene (210 ml), dropwise over 1.5 hours keeping the temperature at 15°–20° C. The resulting brown mixture was filtered to remove triethylamine hydrochloride as a white amorphous solid. The toluene filtrate was washed in water, dried and evaporated to give 1-chloro-4-piperidino-2-naphthol (of structure 3a below) as a brown viscous oil (61.80 g;77% purity by gel permeation chromatography;91% yield based on 2-naphthol). Distillation gave the naphthol as a viscous amber gum B.Pt 150° C./0.3 mmHg.

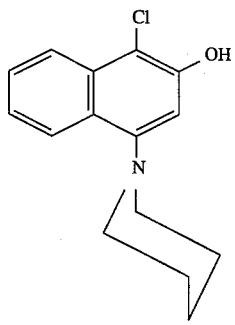

(b) 4-Piperidino-2-naphthol

1-Chloro-4-piperidino-2-naphthol (3.0 g;0.0115 mol), prepared as in 1(a) above, dissolved in 1.25M aqueous NaOH (100 ml) was stirred and heated to 75°–80° C. To the solution was added (50/50) Raney Nickel (14.0 g) portionwise over 1 hour. The mixture was stirred for 1.5 h, cooled then filtered through celite with washing (3×2M NaOH). The filtrate was neutralised with conc. HCl and extracted into $CH_2Cl_2$, dried and evaporated to yield crude 4-piperidino-2-naphthol (1.46 g;56%) as a red-orange oil. Purification by flash chromatography over silica ($CH_2Cl_2$) gave 4-piperidino-2-naphthol (of structure 4a below) as a red oil.

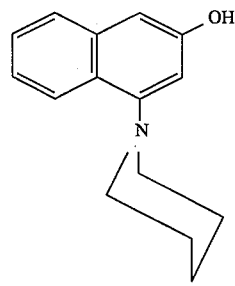

(c) A mixture of 4-piperidino-2-naphthol (1.00 g; 0.0044 mol), prepared as described in 1(b) above, 1,1-dianisylprop-2-yn-1-ol(1.18 g;0.0044 mol), acidic alumina Brockmann 1 (4 g) and toluene (40.0 ml) was heated and stirred for 1.5 h, cooled and filtered. The filtrate was washed with 2M NaOH then water, dried and evaporated to give a red gum. Purification of the gum by flash chromatography over silica (20% ethylacetate in hexane) afford an orange gum which upon trituration with pet. ether (40–60)/diethyl ether yielded 3,3-dianisyl-6-piperidino -3H-naphtho[2,1-b]pyran (of structure 5a below) as an off-white solid (5% yield), m.pt. 114°–119° C.

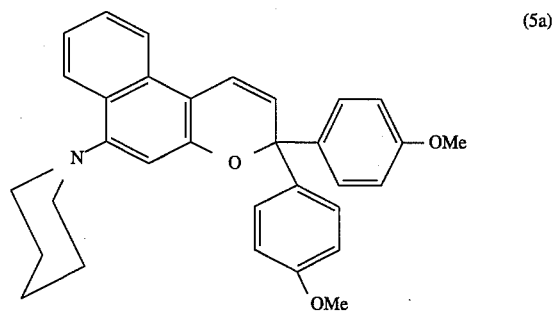

EXAMPLE 2

1,3,3-Trimethyl-6'-morpholinospiro[indoline-2,3'-[3H]-naphtho[2,1-b]pyran].

(a) 1-Chloro-4-morpholino-2-naphthol

2-Naphthol (28.8 g; 0.200 mol) was dissolved in toluene (200 ml) by warming. The pale brown solution was cooled and vigorously stirred until the naphthol began to precipitate and chlorine (31.29 g;0.442 mol) was then passed through the solution at approximately 2.5–3.0 g/min followed immediately by nitrogen gas. The resulting amber solution was treated firstly with triethylamine (24.68 g;0.244 mol) in one portion and then with a solution of morpholine (17.40 g;0.20 mol) in toluene (180 ml) dropwise over 1.5 hours keeping the temperature at 15°–20° C. The resulting brown mixture was filtered to remove triethylamine hydrochloride as a white amorphous solid. The toluene filtrate was washed with water, dried and evaporated to give 1-chloro-4-morpholino-2-naphthol as a brown viscous oil (57.76 g). Purification by chromatography over silica (eluent: 15% ethyl acetate in toluene) gave the product as an off-white solid (34.37 g;65%). Further purification by crystallisation from toluene gave the product as a white solid, m.pt. 163°–65° C.

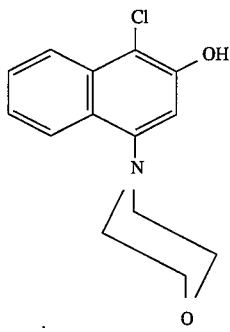

(b) 4-Morpholino-2-naphthol

1-Chloro-4-morpholino-2-naphthol (15.0 g;0.057 mol), prepared as described in 2(a) above, was dissolved in 10% aqueous potassium hydroxide (100 ml) and was treated in the presence of palladium on charcoal (1.75 g;5%) at room temperature under 3 atmospheres of hydrogen until a stoichiometric amount of hydrogen was absorbed (approximately 24h). The palladium catalyst was removed by filtration and the filtrate neutralised with glacial acetic acid to afford 4-morpholino-2-naphthol as a white solid (8.5 g;65%), m.pt. 231°–232° C.

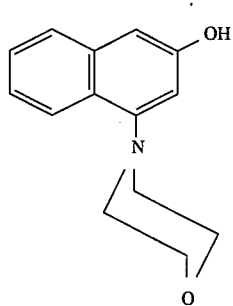

(c) A mixture of 4-morpholino-2-naphthol (0.47 g;0.002 mol), prepared as in 2(b) above, 1,3,3-trimethyl-2-methyleneindole (0.8 g;0.0022 mol) and triethylorthoformate (10.0 ml) was stirred under nitrogen and heated to reflux for 18 hrs. The resulting purple solution was cooled and evaporated to remove the excess triethylorthoformate and the residue flash chromatographed over silica (40% diethyl ether in hexane) to yield an orange gum (0.28 g; yield 34%). Trituration of the gum with diethyl ether afforded the 1,3,3-trimethyl-6'-morpholinospiro [indoline-2,3'-[3H]-naphtho[2,1-b]pyran having the structure shown below as a pale brown solid, m.pt 191°–194° C.

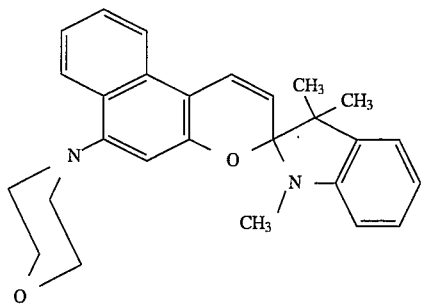

EXAMPLE 3

3,3-Dianisyl-6-morpholino-3H-naphtho[2, 1-b]pyran

4-Morpholino-2-naphthol was prepared as described in Example 2(b). A mixture of 4-morpholino-2-naphthol (0.50 g;0.0022 mol), 1,1-dianisylprop-2-yn-1-ol (0.59 g; 0.0022 mol), acidic alumina Brockmann 1(4 g) and toluene (35.0 ml) was heated and stirred for 1.5 h, cooled, filtered and the solid washed with toluene. The filtrate was evaporated to give an orange crystalline solid which was washed with diethyl ether to give 3,3-dianisyl -6-morpholino-3H-naphtho [2,1-b]pyran as a white solid (0.61 g;58% yield), m.pt. 211°–213° C.

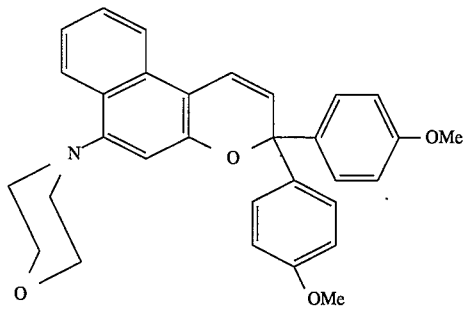

EXAMPLE 4

3-Anisyl-3-(4-trifluoromethyl)phenyl-6-morpholino -3H-naphtho[2,1-b]pyran.

4-Morpholino-2-naphthol was prepared as described in Example 2(b). A mixture of 4-morpholino-2-naphthol (0.23 g;0.001 mol), 1-anisyl-1-(4-trifluoromethyl) phenylprop-2-yn-1-ol (0.29 g;0.001 mol), acidic alumina Brockmann 1 (3 g) and toluene (40.0 ml) was heated and stirred for 1.5 h, cooled, filtered and the solid washed with toluene. The filtrate was evaporated to give a pale orange crystalline solid which was washed with diethyl ether to give 3-anisyl-3-(4-trifluoromethyl)phenyl -6-morpholino-3H-naphtho[2,1-b] pyran as a white solid (0.12 g;24% yield), m.pt. 226°–228° C.

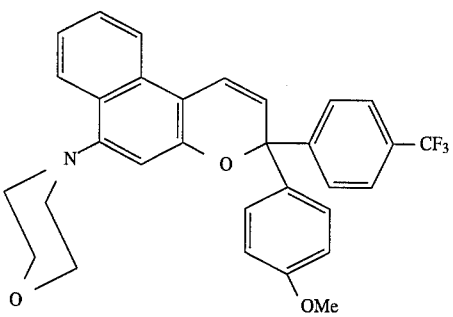

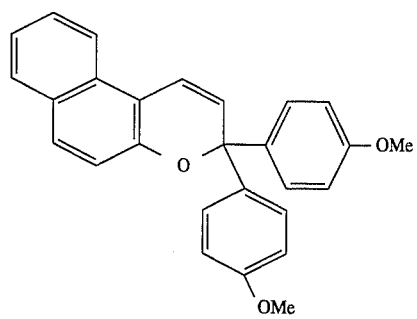

EXAMPLE 5

3-Anisyl-3-(2,4-dimethoxyphenyl)6-morpholino-3H-naphtho [2,1-b]pyran.

4-Morpholino-2-naphthol was prepared as described in Example 2(b). A mixture of 4-morpholino-2-naphthol (0.25 g;0.0011 mol), 1-anisyl-1-(2,4-dimethoxy) phenylprop-2-yn-1-ol (0.33 g;0.0011 mol), acidic alumina Brockmann 1(3 g) and toluene (40.0 ml) was heated and stirred for 1.5 h, cooled, filtered and the solid washed with toluene. The filtrate was evaporated and chromatographed over silica (eluent: 40% ethylacetate in hexane) to give a dark brown gum which was washed with pet. ether (30–40) to give 3-anisyl-3-(2,4-dimethoxy) phenyl-6-morpholino -3H-naphtho[2,1-b]pyran as a white solid (0.10 g;18% yield), m.pt. 163°–165° C.

COMPARATIVE EXAMPLE 2

3-Anisyl-3-(p-trifluoromethyl)phenyl-3H-naphtho[2,1-b] pyran.

A mixture of 2-naphthol (1.44 g;0.010 mol), 1-anisyl-1-(4-trifluoromethyl)phenylprop-2-yn-1-ol (3.22 g;0.0105 mol), acidic alumina Brockmann 1 (8 g) and benzene (40.0 ml) was heated and stirred for 3 h, cooled, filtered and the solid washed with toluene. The filtrate was evaporated to give an orange oil which was chromatographed over silica (eluent: 10% ethylacetate in pet. ether (40–60)) to give a pale yellow oil which solidified on trituration with diethyl ether to yield 3-anisyl-3-(4-trifluoromethyl)phenyl -3H-naphtho[2,1-b]pyran as a white solid (1.60 g;37% yield), m.pt. 136°–137.5° C.

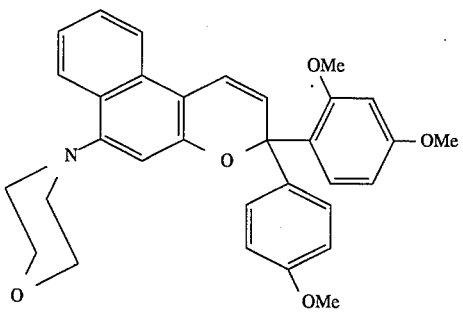

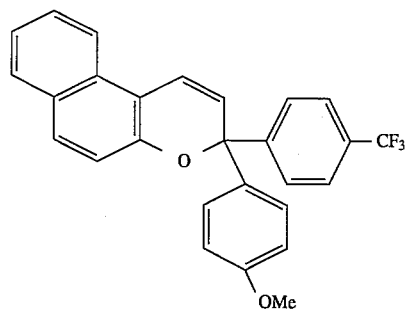

For the purposes of comparison a number of corresponding compounds having no substitution at the 6-position were also prepared. The preparation of these compounds is described in the following Comparative Examples.

COMPARATIVE EXAMPLE 1

3,3-Dianisyl-3H-naphtho[2,1-b]pyran.

A mixture of 2-naphthol (3.23 g;0.0224 mol), 1,1-dianisylprop-2-yn-1-ol (6.00 g;0.0224 mol), acidic alumina Brockmann 1(6 g) and toluene (250 ml) was heated and stirred for 1.5 h, cooled, filtered and the solid washed with toluene. The filtrate was evaporated to give a pale purple tacky solid which was washed with pet. ether (40–60)/ diethyl ether to yield crude product (7.07 g). Purification of the solid by crystallisation from ethylacetate gave 3,3-dianisyl-3H-naphtho[2,1-b]pyran as a white solid (5.52 g;66% yield), m.pt 176°–177° C.

COMPARATIVE EXAMPLE 3

3-Anisyl-3-(2,4-dimethoxyphenyl)-3H-naphtho[2,1-b] pyran.

A mixture of 2-naphthol (0.48 g;0.00335 mol), 1-anisyl-1-(2,4-dimethoxy)phenylprop-2-yn-1-ol (1.00 g; 0.00335 mol), acidic alumina Brockmann 1 (2 g) and toluene (40.0 ml) was heated and stirred for 2 h, cooled, filtered and the solid washed with toluene. The filtrate was evaporated and chromatographed over silica (eluent; 20% ethylacetate in hexane) to give an orange oil which was washed with pet. ether (60–80)/diethyl ether to give the crude product as an off-white solid which was crystallised from ethylacetate/ hexane to give 3-anisyl-3-(2,4-dimethoxy) phenyl-3H-naphtho[2,1-b]pyran as a white solid (0.77 g;56% yield), m.pt. 140°–143° C.

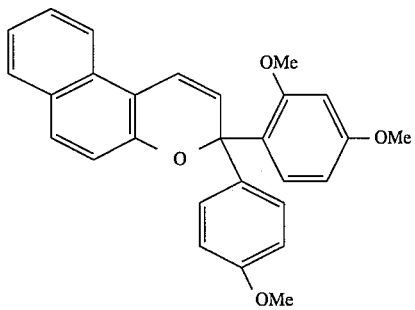

The photochromic properties of the naphthopyran compounds of the present invention were tested by preparing, in conventional manner, by a direct casting process, 2.4 mm plates of a U.V. curable plastics host material (made and sold as SPECTRALITE by Sola Optical USA) incorporating the photochromic naphthopyran in a concentration of 0.05% w/w.

Similar plates were made with samples of the comparative compounds.

The resultant plates were illuminated under standard solar simulation conditions at Air Mass 2 at 21° C. (see Parry Moon, J. Franklin Inst. 230, (1940), p 583–617). The measurements which were made on the samples in the darkened condition were taken when the samples had reached a steady state; this steady state was deemed to have been reached after 10 minutes in the darkened condition.

The results obtained are shown in Table 1 below.

TABLE 1

|  | Bleached IVT | Darkened IVT | IOD $\lambda$ max | $\lambda$ max nm |
|---|---|---|---|---|
| Examples |  |  |  |  |
| 1 | 86.1 | 58.3 | 1.95 | 452 |
| 3 | 87.4 | 58.4 | 1.57 | 452 |
| 4 | 90.4 | 75.4 | 1.72 | 432 |
| 5 | 79.5 | 48 | 2.39 | 432 |
| Comparative Examples |  |  |  |  |
| 1 | 91.2 | 79.9 | 0.12 | 490 |
| 2 | 91.2 | 84.0 | 0.15 | 450 |
| 3 | 89.9 | 54.8 | 0.69 | 488 |

The results in Table 1 show the integrated visible transmission (IVT) measured in both the bleached condition and the darkened condition. These values show, for each material, the typical visual photochromic range which can be achieved.

These IVT values enable one to calculate the induced optical density at the point of maximum adsorption of the chromophore (IOD at $\lambda$ max) by means of the following relationship:

$$\text{IOD at } \lambda \text{ max} = \log_{10} \frac{\text{Bleached } IVT}{\text{Darkened } IVT}$$

The results obtained are set out in Table 1. The relatively high IOD values obtained with the naphthopyran compounds of the present invention (ranging from 1.57 to 2.39) demonstrate the very dense colouring which is obtained with the photochromic materials of the present invention. These results contrast markedly with the low IOD values obtained with the comparative samples (ranging from 0.12 to 0.69).

The photochromic naphthopyran compounds of the present invention are also found to exhibit very good fatigue resistance, that is to say that the naphthopyran compounds of the present invention are found, in general, to be capable of maintaining their good photochromic properties and intense dark colouration in the darkened state over relatively long periods of time without undergoing any substantial degree of degradation.

In addition to the intermediates described in Examples 1(a), 1(b) and 2(a) and 2(b), the following intermediate compounds were also prepared:

EXAMPLE 6

(a) 1-Chloro-4-pyrrolidino-2-naphthol

2-Naphthol (14.43 g; 0.100 mol) was dissolved in toluene (200 ml) by warming. The pale brown solution was cooled and vigorously stirred until the naphthol began to precipitate and chlorine (15.22 g;0.21 mol) was then passed through the solution at approximately 2.5–3.0 g/min followed immediately by nitrogen gas. The resulting amber solution was treated firstly with triethylamine (12.12 g;0.12 mol) in one portion and then with a solution of pyrrolidine (7.10;0.10 mol), in toluene (100 ml), dropwise over 1.5 hours keeping the temperature at 15°–20° C. The resulting brown mixture was filtered to remove triethylamine hydrochloride as a white amorphous solid. The toluene filtrate was washed with water, dried and evaporated to give 1-chloro-4-pyrrolidino-2-naphthol as a brown viscous oil (25.87 g). Purification by chromatography over silica (eluent: toluene) gave the product as a red-brown oil (3.825 g;15%).

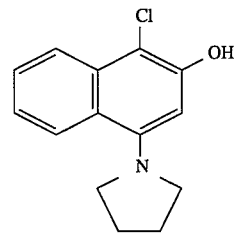

(b) 4-Pyrrolidino-2-naphthol

1-Chloro-4-pyrrolidino-2-naphthol (2.47 g;0.010 mol), prepared as described in Example 6(a), was dissolved in 10% aqueous potassium hydroxide (50 ml) and was treated in the presence of palladium on charcoal (1.00 g;5%) at room temperature under 3 atmospheres of hydrogen until a stoichiometric amount of hydrogen was absorbed (approximately 24h). The palladium catalyst was removed by filtration and the filtrate neutralised with glacial acetic acid. The solution was extracted with dichloromethane (2×50 ml), the extracts combined, dried and evaporated to afford crude 4-pyrrolidino-2-naphthol as an unstable dark oil (0.58 g;27%). The crude product could not be purified further using conventional methods.

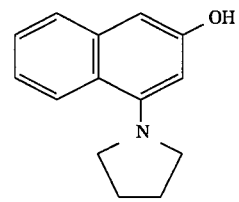

EXAMPLE 7

(a) 1-Chloro-4-indolino-2-naphthol

2-Naphthol (28.8 g; 0.200 mol) was dissolved in toluene (200 ml) by warming. The pale brown solution was cooled and vigorously stirred until the naphthol began to precipitate and chlorine (30.21 g;0.43 mol) was then passed through the solution at approximately 2.5–3.0 g/min followed immediately by nitrogen gas. The resulting amber solution was treated firstly with triethylamine (24.68 g;0.244 mol) in one portion and then with a solution of indoline (23.8 g;0.20 mol), in toluene (200 ml), dropwise over 1.5 hours keeping the temperature at 15°–20° C. The resulting brown mixture was filtered to remove triethylamine hydrochloride as a white amorphous solid. The toluene filtrate was washed with water, dried and evaporated to give 1-chloro-4-indolino-2-naphthol as a brown viscous oil (69.7 g). Purification by chromatography over silica (eluent: 15% dichloromethane in toluene) gave the product as a brown-green oil (43.2 g;73%). Further purification by distillation (170° C./0.1 mmHg) gave the naphthol as a pale brown viscous gum.

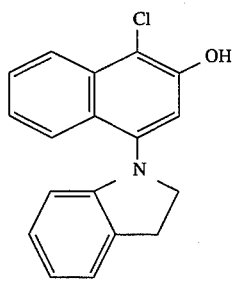

(b) 4-Indolino-2-naphthol

1-Chloro-4-indolino-2-naphthol (5.6 g;0.019 mol), purified as described in Example 7(a), was dissolved in 10% aqueous potassium hydroxide (100 ml) and was treated in the presence of palladium on charcoal (1.75 g;5%) at room temperature under 3 atmospheres of hydrogen until a stoichiometric amount of hydrogen was absorbed (approximately 24h). The palladium catalyst was removed by filtration and the filtrate neutralised with glacial acetic acid. The solution was extracted with dichloromethane (2×50 ml), the extracts combined, dried and evaporated to afford 4-indolino-2-naphthol (3.4 g;69%) as a red-orange oil.

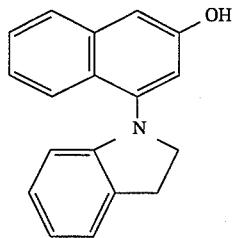

We claim:

1. A naphthopyran compound of general formula (I)

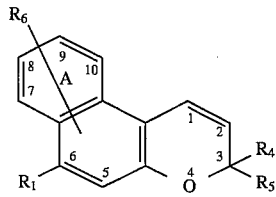

wherein $R_1$ represents a group of the formula $-NR_2R_3$ wherein each of $R_2$ and $R_3$, which may be the same or different, independently represents an alkyl group, or a carbocyclic or heterocyclic group, or $R_2$ and $R_3$ taken together with the nitrogen atom to which they are attached represent a heterocyclic ring having one or more hetero atoms and which may optionally carry at least one substituent selected from alkyl, aryl or heteroaryl groups;

each of $R_4$ and $R_5$, which may be the same or different, independently represents an alkyl, alkenyl, carbocyclic or heterocyclic group, or $R_4$ and $R_5$ taken together with the carbon atom to which they are attached form a carbocyclic ring or a heterocyclic ring; and $R_6$ represents a hydrogen atom or a substituent selected from alkyl, alkoxy, aryl, aryloxy, heteroaryl, halogen, a group of formula $R_1$ as defined above, azo, imino, amide, carboxylate, ester, cyano, trifluromethyl or nitro, and in addition $R_6$ may represent a carbocyclic or heterocyclic ring fused to ring A.

2. A naphthopyran compound according to claim 1, wherein the $R_1$ substituent is a piperidino group.

3. A naphthopyran compound according to claim 1, wherein the $R_1$ substituent is a morpholino group.

4. A naphthopyran compound according to claim 1, wherein the $R_4$ and $R_5$ substituents are chosen from a phenyl group, a 4-trifluoromethylphenyl group, a 4-alkoxyphenyl group, a 2,4-di(alkoxy)phenyl group or a 4-dialkylaminophenyl group.

5. A naphthopyran compound according to claim 4, wherein the $R_4$ and $R_5$ substituents are chosen from a 4-methoxyphenyl group, a 2,4-dimethoxyphenyl group or a 4-dimethylaminophenyl group.

6. A naphthopyran compound according to claim 1, wherein the $R_4$ and $R_5$ substituents together with the carbon atom to which they are attached form a spiro-indoline group carrying alkyl or aryl substituents or alicyclic $C_{1-18}$ groups at the 1-, 3-, 3-positions of the indoline ring.

7. A naphthopyran compound according to claim 6, wherein the said alkyl groups are linear or branched $C_{1-18}$ groups.

8. A naphthopyran compound according to claim 6, wherein the aromatic ring of the indoline carries one or more substituents which are substituents as defined for $R_6$ in claim 1.

9. A process for preparing a naphthopyran compound of general formula (I) as defined in claim 1, which process comprises (a) chlorinating a solution of a 2-naphthol of general formula (VI):

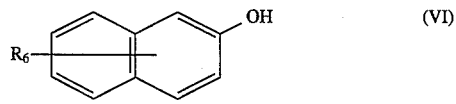

wherein $R_6$ is as defined in claim 1, in an organic solvent to produce the corresponding 1,1-dichloronaphth-2-one which is reacted with an amine of general formula $R_1H$ in the presence of an organic base to generate a chloronaphthol of general formula (III):

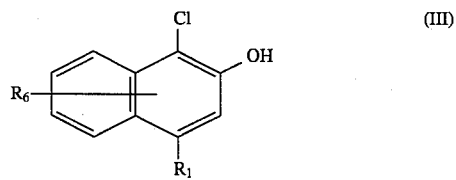

(b) subjecting the chloro-naphthol of general formula (III) to a hydrodehalogenation reaction to produce a substituted naphthol of general formula (IV):

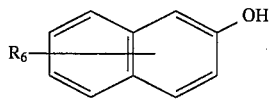 (VI)

and then either:

(c) condensing the substituted naphthol of general formula (IV) with a propargyl alcohol of general formula (V):

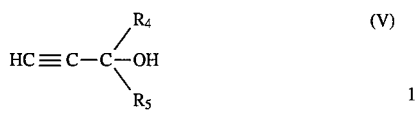 (V)

wherein $R_4$ and $R_5$ are as defined in claim 1, in the presence of acidic alumina, trifluoroacetic acid or another like acidic catalyst, or (c') when $R_4$ and $R_5$ together with the carbon atom to which they are attached form a spiro-indoline group, condensing the substituted naphthol of general formula (IV) with a 2-alkylidene indole of general formula (IX):

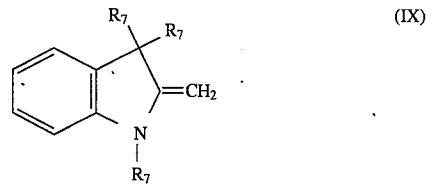 (IX)

wherein $R_7$ represents an alkyl group or an aryl group or an alicyclic $C_{1-18}$ group, in the presence of a trialkyl orthoformate.

10. A photochromic article comprising a polymeric host material having a naphthopyran compound as defined in claim 1 incorporated therein or applied thereto.

11. A photochromic article according to claim 10, wherein the polymeric host material is selected from polymers of polyol (allyl carbonate) monomers, polyacrylates, poly-(alkylacrylates), cellulose acetate, cellulose triacetate, cellulose acetate propionate, cellulose acetate butyrate, poly-(vinyl acetate), poly(vinyl alcohol), polyurethanes, polycarbonates, polyethylene terephthalate, polystyrene, styrene/methylmethacrylate copolymers, styrene/acrylonitrile copolymers, and polyvinylbutyral.

12. A photochromic article according to claim 11, wherein the polymeric host material is a polymer of triethyleneglycol dimethacrylate (TEGDM), or a polymer of diethyleneglycol bis (allyl carbonate).

13. A photochromic article according to claim 10, wherein the amount of naphthopyran compound is from 0.001 to 0.1% by weight, based on the weight of the polymeric host material.

14. A photochromic article according to claim 10, comprising a further photochromic compound selected from spiro(indoline) naphthoxazines, spiro(indolino)pyrido benzoxazines, and spiro(indolino)benzoxazines.

15. A photochromic article according to claim 14, wherein the further photochromic compound is present in an amount of from 0.001 to 0.5% by weight, based on the weight of the polymeric host material.

16. A photochromic article according to claim 10, which is in the form of a lens.

17. A photochromic article according to claim 16, wherein the lens is an ophthalmic lens.

18. A naphthopyran selected from the group consisting of 3,3-Dianisyl-6-piperidino-3H-naphtho[2,1-b] pyran, 3,3-Dianisyl-6-morpholino-3H-naphtho[2,1-b]pyran, 3-Anisyl-3-(p-trifluoromethylphenyl) -6-morpholino-3H-naphtho[2,1-b]pyran, 3-Anisyl-3-(2,4-dimethoxyphenyl)-6-morpholino-3H-naphtho[2,1b]pyran, and 1,3,3-Trimethyl-6'-morpholinosphiro[indoline-2,3'-(3H)-naphtho [2,1-b] pyran].

19. The naphthopyran of claim 18 being 3,3-Dianisyl-6-piperidino-3H -naphtho[2,1-b]pyran.

20. The naphthopyran of claim 18 being 3,3-Dianisyl-6-morpholino-3H-naphtho[2,1-b]pyran.

21. The naphthopyran of claim 18 being 3-Anisyl-3-(p-trifluoromethylphenyl)-6-morpholino-3H-naphtho[2,1-b] pyran.

22. The naphthopyran of claim 18 being 3-Anisyl-3-(2, 4-dimethoxyphenyl) -6-morpholino-3H-naphtho[2,1-b]pyran.

23. The naphthopyran of claim 18 being 1,3,3-Trimethyl-6'-morpholinosphiro [indoline-2,3'-[3H]-naphtho[2,1-b]pyran].

* * * * *